(12) United States Patent
Zhang et al.

(10) Patent No.: US 9,540,687 B2
(45) Date of Patent: Jan. 10, 2017

(54) DNA FRAGMENT DETECTION METHOD, DNA FRAGMENT DETECTION KIT AND THE USE THEREOF

(75) Inventors: Jianguang Zhang, Beijing (CN); Zhongchun Zhou, Beijing (CN); Daixing Zhou, Beijing (CN); Genming Xu, Beijing (CN); Yang Gao, Beijing (CN); Feng Tian, Beijing (CN)

(73) Assignee: BERRY GENOMICS CO., LTD., Beijing (CN)

( * ) Notice: Subject to any disclaimer, the term of this patent is extended or adjusted under 35 U.S.C. 154(b) by 116 days.

(21) Appl. No.: 14/347,113

(22) PCT Filed: Jul. 11, 2012

(86) PCT No.: PCT/CN2012/078461
§ 371 (c)(1),
(2), (4) Date: Mar. 25, 2014

(87) PCT Pub. No.: WO2014/008635
PCT Pub. Date: Jan. 16, 2014

(65) Prior Publication Data
US 2014/0234850 A1    Aug. 21, 2014

(51) Int. Cl.
*C12Q 1/68* (2006.01)

(52) U.S. Cl.
CPC .................................. *C12Q 1/686* (2013.01)

(58) Field of Classification Search
CPC .............. C12Q 1/686; C12Q 2521/501; C12Q 2525/307; C12Q 1/6827; C12Q 2525/191; C12Q 2535/122; C12Q 2565/514; C12Q 1/6883; C12Q 2600/156; C12Q 2600/158; C12Q 2600/16

USPC .......................................................... 435/91.2
See application file for complete search history.

(56) References Cited

U.S. PATENT DOCUMENTS

| | | | |
|---|---|---|---|
| 2009/0311691 A1* | 12/2009 | Drmanac ............... | C12Q 1/682 435/5 |
| 2010/0028888 A1* | 2/2010 | Smith ..................... | C12P 19/34 435/6.14 |

FOREIGN PATENT DOCUMENTS

| | | |
|---|---|---|
| CN | 101967684 | 2/2011 |
| CN | 102181943 | 9/2011 |
| WO | 2010/003316 | 1/2010 |

OTHER PUBLICATIONS

International Search Report issued in corresponding International Application No. PCT/CN2012/078461 on Apr. 18, 2013.

\* cited by examiner

*Primary Examiner* — Cynthia B Wilder
(74) *Attorney, Agent, or Firm* — Whiteford, Taylor & Preston, LLP; Peter J. Davis

(57) ABSTRACT

The disclosure claims a cleaved Deoxyribonucleic acid (DNA) detection method, a DNA fragment detection kit and use thereof. Wherein, the method includes the steps of: designing primers according to a test site or a test region of the DNA fragment; cyclizing the DNA fragment to obtain acyclized DNA; implementing Polymerase Chain Reaction (PCR) amplification for the cyclized DNA by using the primers; and detecting the PCR amplification product. In the disclosure, by cyclizing the DNA fragment, the amplification can be implemented even if only one PCR primer can match with a template, thus, the adaption range and effective template amount of the primer amplification can be greatly increased, and the detection sensitivity of the DNA fragment can be greatly improved.

9 Claims, 5 Drawing Sheets

SEQUENCE LISTING

```
<160> NUMBER OF SEQ ID NOS: 24

<210> SEQ ID NO 1
<211> LENGTH: 17
<212> TYPE: DNA
<213> ORGANISM: Artificial
<220> FEATURE:
<223> OTHER INFORMATION: synthetic

<400> SEQUENCE: 1
gtctcatccc tgcgtgt                                                  17

<210> SEQ ID NO 2
<211> LENGTH: 16
<212> TYPE: DNA
<213> ORGANISM: Artificial Sequence
<220> FEATURE:
<223> OTHER INFORMATION: synthetic
```

```
<400> SEQUENCE: 2
cacgcagggt acgtgt                                                    16

<210> SEQ ID NO 3
<211> LENGTH: 17
<212> TYPE: DNA
<213> ORGANISM: Artificial
<220> FEATURE:
<223> OTHER INFORMATION: synthetic

<400> SEQUENCE: 3
gtctcatccc tgcgtgt                                                   17

<210> SEQ ID NO 4
<211> LENGTH: 16
<212> TYPE: DNA
<213> ORGANISM: Artificial
<220> FEATURE:
<223> OTHER INFORMATION: synthetic

<400> SEQUENCE: 4
cacgcagggt acgtgt                                                    16

<210> SEQ ID NO 5
<211> LENGTH: 16
<212> TYPE: DNA
<213> ORGANISM: Artificial
<220> FEATURE:
<223> OTHER INFORMATION: synthetic

<400> SEQUENCE: 5
tgtgcatggg acgcac                                                    16

<210> SEQ ID NO 6
<211> LENGTH: 17
<212> TYPE: DNA
<213> ORGANISM: Artificial
<220> FEATURE:
<223> OTHER INFORMATION: synthetic

<400> SEQUENCE: 6
tgtgcgtccc tactctg                                                   17

<210> SEQ ID NO 7
<211> LENGTH: 17
<212> TYPE: DNA
<213> ORGANISM: Artificial
<220> FEATURE:
<223> OTHER INFORMATION: synthetic

<400> SEQUENCE: 7
gtctcatccc tgcgtgt                                                   17

<210> SEQ ID NO 8
<211> LENGTH: 17
<212> TYPE: DNA
<213> ORGANISM: Artificial
<220> FEATURE:
<223> OTHER INFORMATION: synthetic

<400> SEQUENCE: 8
acacgtaccc tgcgtgt                                                   17

<210> SEQ ID NO 9
<211> LENGTH: 17
```

-continued

```
<212> TYPE: DNA
<213> ORGANISM: Artificial
<220> FEATURE:
<223> OTHER INFORMATION: synthetic

<400> SEQUENCE: 9
gtctcatccc tgcgtgt                                                    17

<210> SEQ ID NO 10
<211> LENGTH: 17
<212> TYPE: DNA
<213> ORGANISM: Artificial
<220> FEATURE:
<223> OTHER INFORMATION: synthetic

<400> SEQUENCE: 10
acacgcaggg tacgtgt                                                    17

<210> SEQ ID NO 11
<211> LENGTH: 17
<212> TYPE: DNA
<213> ORGANISM: Artificial
<220> FEATURE:
<223> OTHER INFORMATION: synthetic

<400> SEQUENCE: 11
cagagtaggg acgcaca                                                    17

<210> SEQ ID NO 12
<211> LENGTH: 17
<212> TYPE: DNA
<213> ORGANISM: Artificial
<220> FEATURE:
<223> OTHER INFORMATION: synthetic

<400> SEQUENCE: 12
tgtgcgtccc atgcaca                                                    17

<210> SEQ ID NO 13
<211> LENGTH: 123
<212> TYPE: DNA
<213> ORGANISM: human

<400> SEQUENCE: 13
cttgtggagc tcttacacc cagtggagaa gctcccaacc aagctctctt gaggatcttg      60
aaggaaactg aattcaaaaa gatcaaagtg ctgggctccg gtgcgttcgg cacggtgtat    120
aag                                                                 123

<210> SEQ ID NO 14
<211> LENGTH: 381
<212> TYPE: DNA
<213> ORGANISM: human

<400> SEQUENCE: 14
caagtgccgt gtcctggcac ccaagcccat gccgtggctg ctggtccccc tgctgggcca     60
tgtctggcac tgcttttcag catggtgagg gctgaggtga cccttgtctc tgtgttcttg    120
tcccccccag cttgtggagc tcttacacc cagtggagaa gctcccaacc aagctctctt    180
gaggatcttg aaggaaactg aattcaaaaa gatcaaagtg ctgggctccg gtgcgttcgg    240
cacggtgtat aaggtaaggt ccctggcaca ggcctctggg ctgggccgca gggcctctca    300
tggtctggtg gggagcccag agtccttgca agctgtatat ttccatcatc tactttactc    360
```

-continued

```
tttgtttcac tgagtgtttg g                                             381

<210> SEQ ID NO 15
<211> LENGTH: 20
<212> TYPE: DNA
<213> ORGANISM: Artificial
<220> FEATURE:
<223> OTHER INFORMATION: synthetic

<400> SEQUENCE: 15
gctgaggtga cccttgtctc                                                20

<210> SEQ ID NO 16
<211> LENGTH: 19
<212> TYPE: DNA
<213> ORGANISM: Artificial
<220> FEATURE:
<223> OTHER INFORMATION: synthetic

<400> SEQUENCE: 16
cctcaccatg ctggaaagc                                                 19

<210> SEQ ID NO 17
<211> LENGTH: 20
<212> TYPE: DNA
<213> ORGANISM: Artificial
<220> FEATURE:
<223> OTHER INFORMATION: synthetic

<400> SEQUENCE: 17
gctgaggtga cccttgtctc                                                20

<210> SEQ ID NO 18
<211> LENGTH: 19
<212> TYPE: DNA
<213> ORGANISM: Artificial
<220> FEATURE:
<223> OTHER INFORMATION: synthetic

<400> SEQUENCE: 18
cctcaccatg ctggaaagc                                                 19

<210> SEQ ID NO 19
<211> LENGTH: 20
<212> TYPE: DNA
<213> ORGANISM: Artificial
<220> FEATURE:
<223> OTHER INFORMATION: synthetic

<400> SEQUENCE: 19
gctgaggtga cccttgtctc                                                20

<210> SEQ ID NO 20
<211> LENGTH: 19
<212> TYPE: DNA
<213> ORGANISM: Artificial
<220> FEATURE:
<223> OTHER INFORMATION: synthetic

<400> SEQUENCE: 20
cctcaccatg ctggaaagc                                                 19

<210> SEQ ID NO 21
<211> LENGTH: 200
<212> TYPE: DNA
<213> ORGANISM: human
```

```
<400> SEQUENCE: 21
atgctctgct tctgtactgc cagtggatgt gcagacacta aactcatctg ggccaccgtt      60
tggaaagcta gtggttcaga gttctataga ttctagtgca ttcaagcaca atggcacggt     120
tgaatgtaag gcttacaacg atgtgggcaa gacttctgcc tatgcctatt ttaactttgc     180
atttaaaggt aacaacaaag                                                 200

<210> SEQ ID NO 22
<211> LENGTH: 538
<212> TYPE: DNA
<213> ORGANISM: human

<400> SEQUENCE: 22
ctcctctgcc ttctcttccc cagtgctttt ttcactcact aggtcaccaa agtgcttatt      60
cttagacact tgtaaaagga cattttctgt tgattatgaa cctctaactt tgttttaaaa     120
gtatgccaca tcccaagtgt tttatgtatt tatttatttt cctagagtaa gccagggctt     180
ttgttttctt ccctttagat gctctgcttc tgtactgcca gtggatgtgc agacactaaa     240
ctcatctggg ccaccgtttg gaaagctagt ggttcagagt tctatagatt ctagtgcatt     300
caagcacaat ggcacggttg aatgtaaggc ttacaacgat gtgggcaaga cttctgccta     360
tgcctatttt aactttgcat ttaaaggtaa caacaaggt atatttcttt ttaatccaat      420
ttaaggggat gtttaggctc tgtctaccat atcagtcatg attttaagtt cattccaaca     480
ttgaccatgt catttctggt aatacatgca tcacaccata ctgtcatcaa actcacta      538

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
aacgatgtgg gcaagacttc tgc                                             23

<210> SEQ ID NO 24
<211> LENGTH: 23
<212> TYPE: DNA
<213> ORGANISM: Artificial
<220> FEATURE:
<223> OTHER INFORMATION: synthetic

<400> SEQUENCE: 24
aagccttaca ttcaaccgtg cca                                             23
```

DNA FRAGMENT DETECTION METHOD, DNA FRAGMENT DETECTION KIT AND THE USE THEREOF

BACKGROUND OF THE INVENTION

Field of the Invention

The disclosure relates to the field of molecular biology, and in particular to a cleaved Deoxyribonucleic acid (DNA) detection method, a DNA fragment detection kit and the use thereof.

Background

Scientific researchers need to extract DNA from different tissue samples in the molecular biology research. Wherein, the body fluid contains the fragmented DNAs, and the detection of the fragmented DNA is an important step for the molecular biology research. For example, the plasma DNA, also called as the circulating DNA, is the extracellular DNA in the blood, of which the length is tens to hundreds of nucleotides (the main peak is approximately 167 bp); the plasma DNA can exist in the form of DNA-protein complex, and also can be free DNA fragments. The plasma DNA is derived from the DNA release of a small amount of aging dead cells. The generation and removal of the plasma DNA are in a dynamic balance status, and are maintained in a relatively constant low level; 1 mL of the plasma approximately includes the amount of 2000 genomic DNA, namely, the content is extremely low, thus the gene information cannot be detected by adopting the Polymerase Chain Reaction (PCR) in the prior art.

In addition, the source of fresh tissue samples is limited, the Formalin Fixed Paraffin Embedded (FFPE) method solves the problem that the fresh tissues are hard to be stored for a long time, but during the preparation and storage process of the FFPE tissue samples, the tissue is fixed by formalin and embedded by paraffin which is easy to cause cross-linking and fragmentation of the DNA, which is 100 bp-3000 bp fragments, the scientific researchers are hard to obtain enough DNA samples with high quality for high-sensitive detection. At present, a large amount of samples in the world are processed by the FFPE method, and the tissue samples have become one of the most normal biological resources for the scientific research.

The traditional method of detecting whether the DNA fragment has base mutation or other mutations mainly implements detection by implementing PCR amplification for the specific test region. The traditional PCR technology usually adopts a pair of primers which cross two sides of the target region, takes the DNA as a template, which is a method for in vitro enzymatic synthesis of specific DNA fragments. high temperature denaturation, low temperature annealing (renaturation), optimum temperature extension and the like form a period, which circularly operate, so as to make the target DNA be rapidly amplified; the technology has characteristic of high specificity, high sensitivity, simple operations, time-saving property and the like, and is widely applied in fundamental research of gene isolation, cloning and nucleotide sequence analysis, and the diagnosis of diseases. But the PCR technology requires that the DNA template between a pair of primers has no fragmentation point, which provides a great challenge for the seriously-fragmented DNA templates. As the traditional PCR amplification requires that the amplified region is kept complete, the traditional method has low detection sensitivity for the DNA fragment, which limits the application thereof in detecting the DNA fragment samples.

SUMMARY OF THE INVENTION

The disclosure aims at providing a DNA fragment detection method, a DNA fragment detection kit and the use thereof, in order to solve the technical problem of low detection sensitivity of the DNA fragment in the prior art.

In order to achieve the above object, according to one aspect of the disclosure, a DNA fragment detection method is provided. The method includes steps of: designing primers according to a test site or a test region of the DNA fragment; cyclizing the DNA fragment to obtain a cyclized DNA; implementing PCR amplification for the cyclized DNA by using the primers; and detecting the PCR amplification product.

Further, the primers are a primer pair including adjacent primer pair which extends backwards.

Further, the primers of the primer pair which extend backwards are all located on the 5' end or 3' end of the test site or the test region of the DNA fragment.

Further, the interval between the primers of the primer pair which extend backwards is 0-½ of the total base pairs of the DNA fragment.

Further, the interval between the primers of the primer pair which extend backwards is 0-50 base pairs.

Further, the interval between the primers of the primer pair which extend backwards is 0-10 base pairs.

Further, the bases on the 5' end of the primers of the primer pair which extend backwards are overlapped partly.

Further, the primers are one primer.

Further, before cyclizing the DNA fragment, the method further includes the step of pre-amplifying the DNA fragment.

Further, cyclization is CIRCLIGASE mediated double-chain DNA cyclization.

Further, the DNA fragment includes the plasma free DNA, urine free DNA, sweat free DNA, saliva free DNA, or the DNA extracted from FFPE tissues.

Further, the test site or the test region of the DNA fragment include insertion, deletion, substitution or fusion gene mutation.

According to another aspect of the disclosure, a DNA fragment detection kit is provided. The kit includes: a DNA extraction reagent, a DNA cyclase, target DNA amplification primers and an amplification reagent.

Further, the kit includes: target DNA pre-amplification primers and a pre-amplification reagent.

Further, the target DNA amplification primers are a primer pair including adjacent primers which extend backwards.

Further, the primers of the pair which extend backwards are all located on the 5' end or 3' end of the test site or the test region of the DNA fragment.

Further, the interval between the primers of the primerpair which extend backwards is ½ of the total base pairs of the DNA fragment.

Further, the interval between the primers of the primer pair which extend backwards is 0-50 base pairs.

Further, the interval between the primers of the primer pair which extend backwards is 0-10 base pairs.

Further, the bases on the 5' end of the primers of the primer pair which extend backwards are overlapped partly.

Further, the primers are one primer.

Further, the test site or the test region of the DNA fragment includes insertion, deletion, substitution or fusion gene mutation.

According to another aspect of the disclosure, the use of the DNA fragment detection kit in detecting cancers, congenital monogenic diseases, chromosomal aberration diseases and infectious diseases are provided.

According to another aspect of the disclosure, the use of the DNA fragment detection kit in vitro detection of DNA mutations is provided.

The traditional method for detecting the DNA fragment mainly includes implementing PCR amplification for the test region, and then implementing detection. As PCR primers are set on two sides of the test region, the test region is required to keep complete; and as the DNA fragment is generated by random fragmentation, the test region of most DNA fragment are incomplete; only a small amount of the DNA fragment can be used as the amplification template, and PCR can hardly detect. In the disclosure, cyclization for the DNA fragment is firstly implemented, and then the amplification can be implemented even when only one PCR primer can match with the template; thus, the adaption range and effective template amount of the primer amplification can be greatly increased, and the detection sensitivity of the DNA fragment can be greatly improved.

BRIEF DESCRIPTION OF THE DRAWINGS

The descriptions and drawings are used for further understanding the disclosure, and forming a part of the disclosure; the exemplary embodiments of the disclosure and the descriptions thereof are used for explaining the disclosure, without improperly limiting the disclosure. In the drawings.

DETAILED DESCRIPTION OF THE INVENTION

It should note that the embodiments of the disclosure and the characteristics of the embodiments can be mutually combined without conflicts. The disclosure is described below with reference to the drawings and the embodiments in details.

The "DNA fragment" called in the disclosure refers to the short fragment DNA which is formed by random fragmentation of biological genomic DNA, and has the length of 20-2000 bp approximately.

According to one typical embodiment, the disclosure provides a DNA fragment detection method, including the steps of: 1) designing primers according to a test site or a test region of the DNA fragment; 2) cyclizing the DNA fragment to obtain a cyclized DNA; 3) implementing PCR amplification for the cyclized DNA by using the primers; and 4) detecting the PCR amplification product. The traditional method for detecting the DNA fragment mainly includes implementing PCR amplification for the test region, and then implementing detection. As PCR primers are set on two sides of the test region, the test region is required to keep complete; and as the DNA fragment is generated by random fragmentation, the test region of most DNA fragment are incomplete; only a small amount of the DNA fragment can be used as the amplification template, and the PCR can hardly detect. In the disclosure, cyclization for the DNA fragment is firstly implemented, and then the amplification can be implemented even when only one PCR primer can match with the template; thus, the adaption range and effective template amount of the primer amplification can be greatly increased, and the detection sensitivity of the DNA fragment can be greatly improved.

Figure 1:
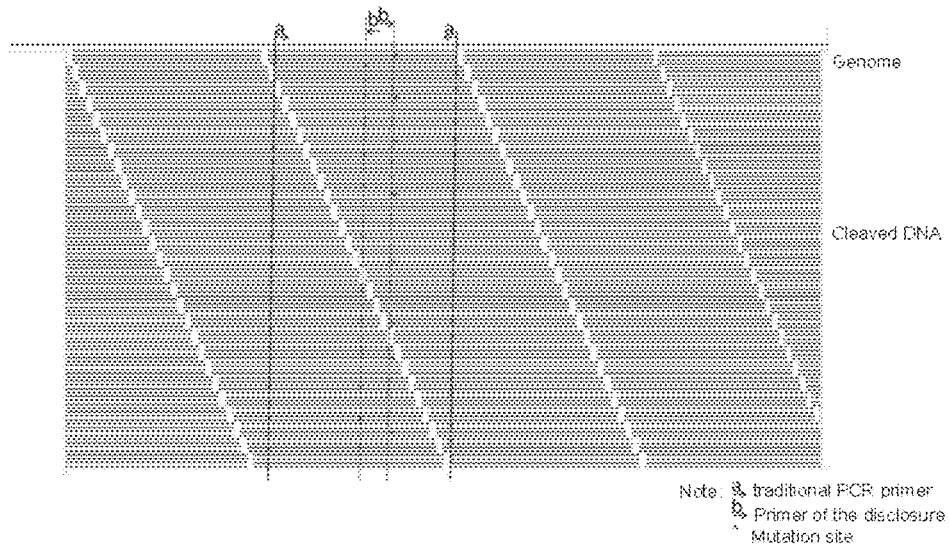
FIG. 1 shows a design principle of the disclosure.

According to one typical embodiment of the disclosure, the primer of the disclosure is a primer pair including adjacent primers which extend backwards. FIG. 1 shows a design principle of the disclosure; suppose that the genome is equally fragmented, a is a traditional primer, the available template is a DNA fragment without fragmentation point between solid lines, b is a primer of the disclosure, and the available template is a DNA fragment without fragmentation point between dotted lines; and this shows that the number of templates capable of being used by the primer designed by the disclosure is much higher than the traditional method.

Figure 2:
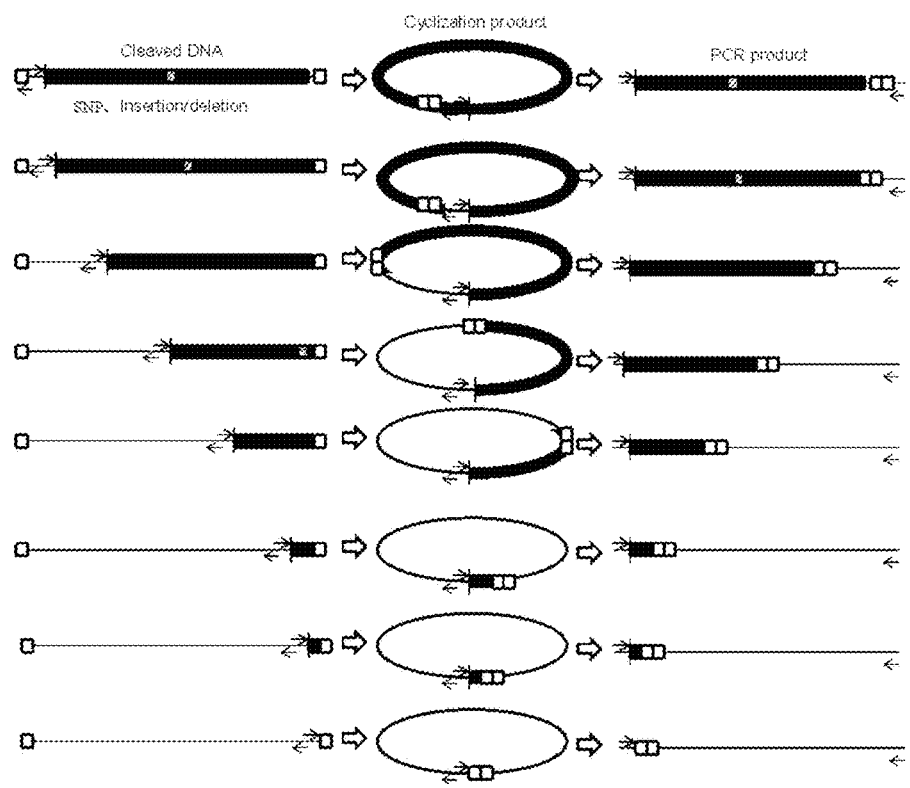
FIG. 2 shows a detection principle aiming at the mutation site of the disclosure.

FIG. 2 shows a detection principle aiming at the mutation site. The left side is the DNA fragment which contains specific back-to-back primer, the block diagrams on two ends represent the annealing region of the pre-amplification primers, the slash block-diagram represents the Single Nucleotide Polymorphism (SNP) site, insertion/deletion mutation site, the black block diagram represents the test region. As the positions of the fragmentation points of the DNA fragment are different, the positions of the back-to-back primers, the SNP site and the insertion/deletion mutation site on the DNA fragment (left, middle, right) can be changed, the sizes of the test region also can be changed, but the relative positions there-between are unchanged. The middle represents the sign of the corresponding DNA fragment cyclization product. The right side represents the sign of the PCR product generated after opening cyclization of the corresponding DNA fragment. Such method can use all the DNA fragments which contain the specific back-to-back primers as the template, so it is more optimized than the traditional PCR.

Figure 3:
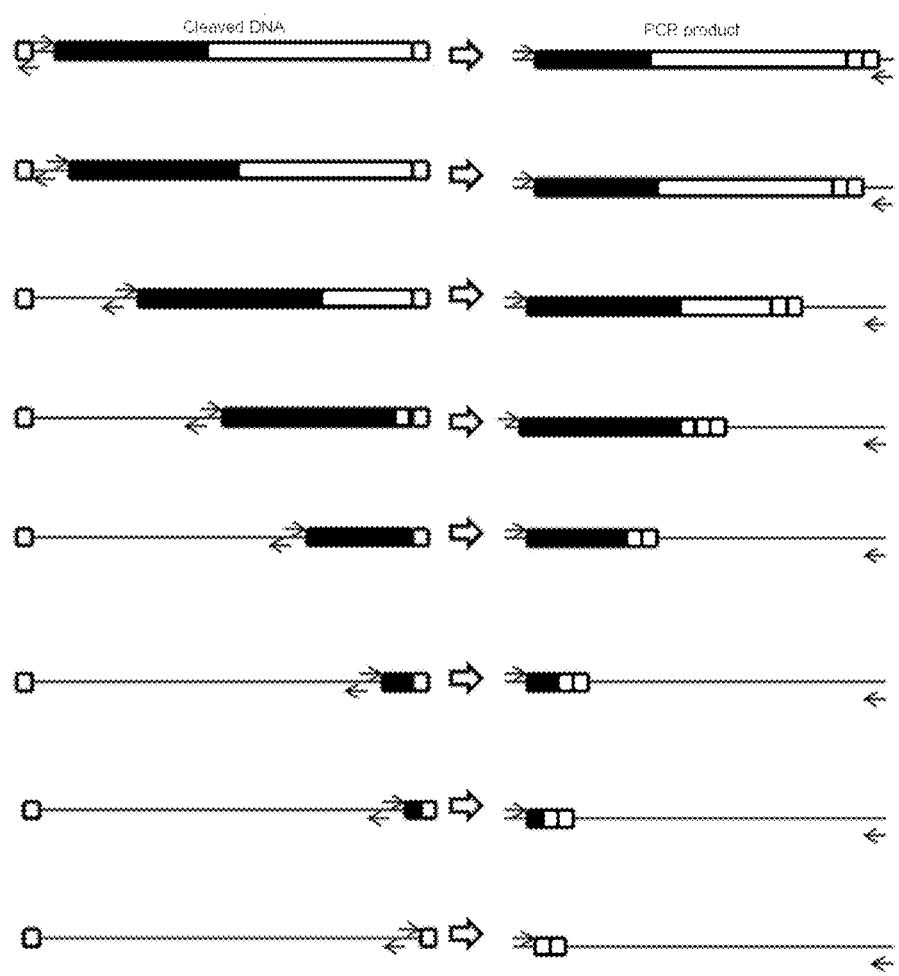
FIG. 3 shows a detection principle aiming at gene fusion of the disclosure.

FIG. 3 shows a detection principle aiming at gene fusion. The left side is the DNA fragment which contains specific back-to-back primer, the block diagrams on two ends represent the annealing region of the pre-amplification primers, gene fusion (back and white, different regions) exists on the downstream of the back-to-back primers. As the positions of the fragmentation points of the DNA fragment are different, the positions of the fusion points on the DNA fragment (left, middle, right) can be changed, but the distance corresponding to the back-to-back primers are unchanged. The right side represents the sign of the PCR product generated after opening cyclization of the corresponding DNA fragment. Such method can use all the DNA fragments which contain the specific back-to-back primers as the template, so it is more optimized than the traditional PCR.

Figure 4:
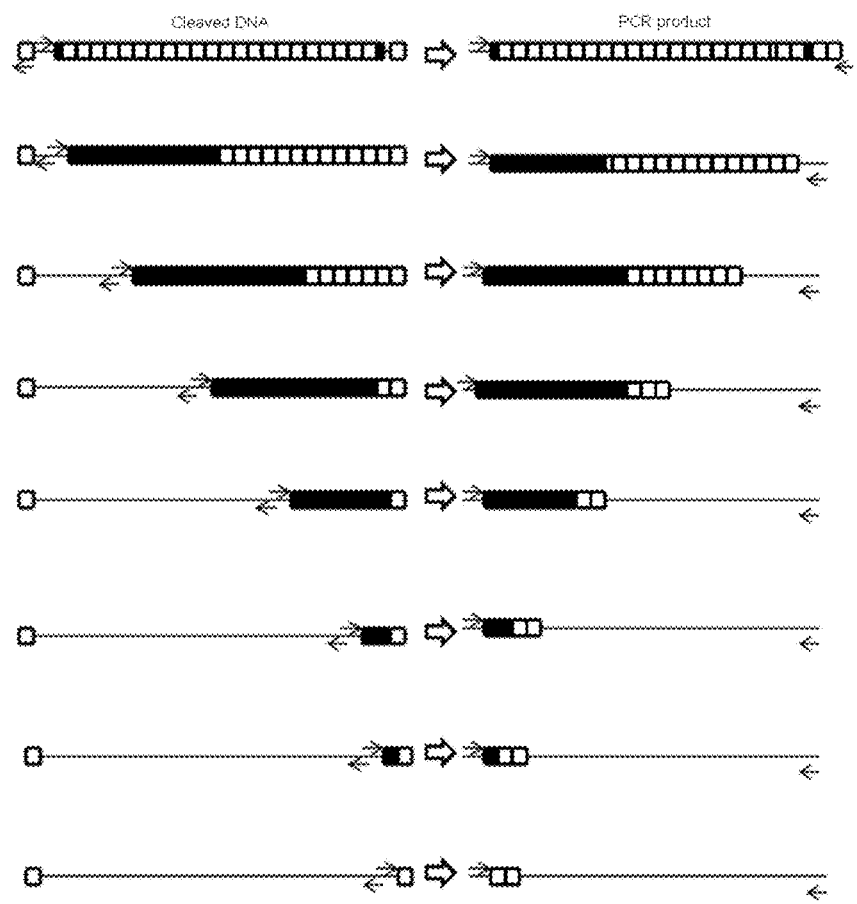
FIG. 4 shows a detection principle of repetition number detection or Short Tandem Repeat (STR) of the disclosure.

FIG. 4 shows a detection principle of repetition number detection or STR of the disclosure. The left side is the DNA fragment which contains specific back-to-back primer, the block diagrams on two ends represent the annealing region of the pre-amplification primers, the repetition region exists on the downstream of the back-to-back primers. As the positions of the fragmentation points of the DNA fragment are different, the repetition times contained by the DNA fragment can be changed, but the repetition times can be judged by detecting the sequence of the repetition region and the two sides. The right side represents the sign of the PCR product generated after opening cyclization of the corresponding DNA fragment.

In conclusion, the above shows that the number of the available DNA templates in the disclosure is higher than the traditional PCR, thus improving the detection sensitivity.

Preferably, the primers which extend backwards are all located on the 5' end or 3' end of the test site or the test region of the DNA fragment.

According to the length of the test region of the DNA fragment and the length of the DNA fragment, the interval between the primers of the primer pair which extend backwards can be 0-½ of the total base pairs of the DNA fragment. After cyclizing the DNA fragment, as the available template number during ½ ring of circumference (number of base pairs) is equal to the traditional PCR of which the length of the amplification product is ½ ring of circumference, and the available template number is much greater than the traditional PCR when being smaller than ½ ring of circumference; the smaller the interval between the primers which extend backwards is, the more the available DNA fragment templates are, and the higher the detection sensitivity is. Preferably, the interval between the primers of the primer pair which extend backwards is 50 base pairs. Further preferably, the interval between the primers of the primer pair which extend backwards is 0-10 base pairs.

The bases on the 5' end of the primers of the primer pair which extend backwards are overlapped partly in the disclosure. And the primer can be one primer according to one typical embodiment of the disclosure. The forward primer in the back-to-back primer pair refers to the primer close to the detection point. When there is one primer, the amplification is transformed to the linear-level amplification from the exponential amplification; the amplification products have different lengths, and all contain the detection site; thus the amplification products can be used for PCR detection.

Figure 5:
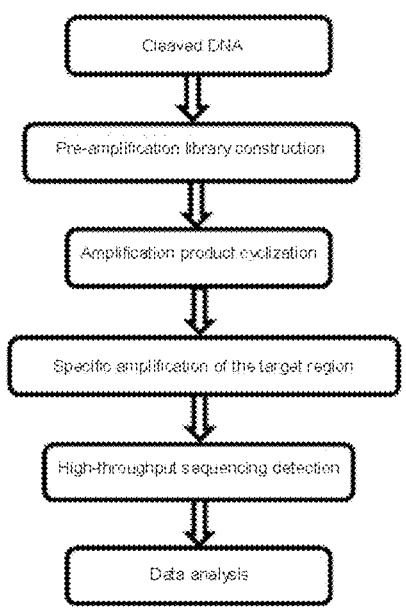
FIG. 5 shows a flowchart of a DNA fragment detection method according to embodiments of the disclosure.

According to the amount of the DNA fragment, the step for pre-amplifying the DNA fragment is added between Step 1) and Step 2) if the amount is too small. FIG. 5 shows a flowchart of a DNA fragment detection method according to an embodiment of the disclosure; pre-amplifying the DNA fragments when the amount of the DNA fragments is not enough, cyclizing the amplification product/DNA fragment, pre-amplifying the detection region by using specific back-to-back primers, and then detecting the amplification product, including the high-throughput sequencing, qPCR and the like, but not limited thereby. Wherein, the pre-amplification can be implemented by the method of connecting the linkers on two ends of the DNA fragment or implementing full genome amplification.

The cyclization of the DNA fragment in the disclosure can adopt any cyclization technology of the prior art, preferably, the cyclization is the CIRCLIGASE mediated double-chain DNA cyclization, which can self-cyclize the single/double-chain DNA/RNA effectively; the cyclization products of the single-chain DNA/RNA are correspondingly introduced in the descriptions, and the experiments shows that it also have efficient self-cyclization effect to the double-chain DNA/RNA. The CIRCLIGASE adopted by the disclosure is the product of Epicentre Company, and the product number is CL9025K, details as www.epibio.com/item.asp?ID=547).

The method of the disclosure can detect the DNA fragment, wherein, it has obvious advantages when detecting the DNA fragment with length of 100-1000 bp. The DNA fragment capable of being detected by the method of the disclosure is the body fluid free DNA, wherein, the body fluid free DNA includes the plasma free DNA, urine free DNA, sweat free DNA, saliva free DNA, or the DNA extracted from formalin-fixed and paraffin-embedded tissues. The plasma free DNA includes but not limited to the plasma free DNA of the cancer patients or pregnant women.

The detection method provided by the disclosure can detect the DNA fragment which contains mutations; wherein the mutation can be homozygous mutation, heterozygous mutation; can be base deletion, base insertion, base substitution; and also can detect the quantitative variation of the somatic mutation, namely, the mutation site; also can be gene fusion; also can be the repetition of the base sequence and the repetition times detected by the method.

According to a typical embodiment, the disclosure provides a DNA fragment detection kit, including: a DNA extraction reagent, a DNA cyclase, target DNA amplification primers and an amplification reagent. Preferably, the kit further includes: target DNA pre-amplification primers and an amplification reagent. Preferably, the target DNA amplification primers are a primer pair including adjacent primer pair which extend backwards. Preferably, the primers of the primer pair which extend backwards are all located on the 5' end or 3' end of the test site or the test region of the DNA fragment. Preferably, the interval between the primers of the primer pair which extend backwards is 0-½ of the base pairs of the DNA fragment. Preferably, the interval between the primers of the primer pair which extend backwards is 0-50 base pairs. Preferably, the interval between the primers of the primer pair which extend backwards is 0-10 base pairs. Preferably, the bases on the 5' end of the primers of the primer pair which extend backwards are overlapped partly. According to a typical embodiment of the disclosure, the target amplification primers is a forward primer, the forward primer in the back-to-back primer pair refers to the primer close to the detection point.

The beneficial effects of the disclosure are further described below with reference to the embodiments, and the experiment conditions in the following embodiments also can be realized via normal methods in the field. All the reagents used in the embodiments all can be contained in the kit of the disclosure.

The CIRCLIGASE adopted in the embodiments 1 and 2 of the disclosure is the product of the Epicentre Company, the product number is CL9025K, details as www.epibio.com/item.asp?ID=547, and other non-marked reagents are commercially available reagents.

Embodiment 1

1. Linker design

Linkers need to anneal to be double-stranded.

```
ssCycADT-1 (SEQ ID NO: 1):
GTCTCATCCCTGCGTGT ssCycADT-2 (SEQ ID NO: 2):
pCACGCAGGGTACGTGT
```

The structure of connection products:

```
Top:
                            (SEQ ID NO: 3)
GTCTCATCCCTGCGTGT (SEQ ID NO: 4)
NNN pCACGCAGGGTACGTGT

Bottom:
                            (SEQ ID NO: 5)
TGTGCATGGGACGCACp (SEQ ID NO: 6)
NNN TGTGCGTCCCTACTCTG Primers:
ssCycUniprimer-F (SEQ ID NO: 7):
pGTCTCATCCCTGCGTGT ssCycUniprimer-R (SEQ ID NO: 8):
pACACGTACCCTGCGTGT Pre-amplified library structure:
                            (SEQ ID NO: 9)
pGTCTCATCCCTGCGTGT (SEQ ID NO: 10)
NNN ACACGCAGGGTACGTGT (SEQ ID NO: 11)
CAGAGTAGGGACGCACA (SEQ ID NO: 12)
NNN TGTGCGTCCCATGCACAp
```

The back-to-back amplification primers of target region aim at Epidermal Growth Factor Receptor (EGFR) exon 18.

Sequence of the EGFR exon 18 is as below (SEQ ID NO: 13):

CTTGTGGAGCCTCTTACACCCAGTGGAGAAGCTCCCAACCAAGCTCTCT

TGAGGATCTTGAAGGAAACTGAATTCAAAAAGATCAAAGTGCTGGGCTC

CGGTGCGTTCGGCACGGTGTATAAG

The EGFR exon 18 and the upstream and downstream thereof contain intron (SEQ ID NO: 14)

CAAGTGCCGTGTCCTGGCACCCAAGCCCATGCCGTGGCTGCTGGTCCCC

CTGCTGGGCCATGTCTGGCACTGCTTTCCAGCATGGTGAGGGCTGAGGT

GACCCTTGTCTCTGTGTTCTTGTCCCCCCCAGCTTGTGGAGCCTCTTAC

ACCCAGTGGAGAAGCTCCCAACCAAGCTCTCTTGAGGATCTTGAAGGAA

ACTGAATTCAAAAAGATCAAAGTGCTGGGCTCCGGTGCGTTCGGCACGG

TGTATAAGGTAAGGTCCCTGGCACAGGCCTCTGGGCTGGGCCGCAGGGC

CTCTCATGGTCTGGTGGGGAGCCCAGAGTCCTTGCAAGCTGTATATTTC

CATCATCTACTTTACTCTTTGTTTCACTGAGTGTTTGG

Specific back-to-back primers:

```
F-1 (SEQ ID NO: 15):
GCTGAGGTGACCCTTGTCTC

R-1 (SEQ ID NO: 16):
CCTCACCATGCTGGAAAGC
```

2. Taking 1 mL of normal human plasma to extract the plasma free DNA.

3. End-blunting

Preparation of reaction mixture in Table 1:

TABLE 1

| | |
|---|---|
| Plasma DNA solution | 38.5 µl |
| T4 DNA phosphorylation buffer (10×) | 5 µl |
| 10 mM dNTP mixture | 2 µl |
| T4 DNA polymerase | 2 µl |
| T4 DNA phosphorylase | 2 µl |
| Klenow enzyme | 0.5 µl |
| Sterile H$_2$O | 0 µl |
| Total volume | 50 µl |

Incubating for 30 min at 20 degrees centigrade;

purifying the DNA samples by a purification column, and eluting the samples with 42 µl of sterile dH$_2$O or elution buffer.

Adding a poly-adenine tail to the 3' end of the DNA fragment;

Preparation of the reaction mixture in Table 2:

TABLE 2

| | |
|---|---|
| Blunt-ended DNA | 32 µl |
| Klenow reaction buffer (10×) | 5 µl |
| dATP solution | 10 µl |
| klenow ex-(3'-5' exonuclease activity deletion) | 3 µl |
| Sterile H$_2$O | 0 µl |
| Total volume | 50 µl |

Incubating for 30 min at 37 degrees centigrade;

purifying the DNA samples by a purification column, and eluting the samples with 25 µl of sterile dH$_2$O or elution buffer.

Connecting a linker to the DNA fragment;

Preparation of the reaction mixture in Table 3:

TABLE 3

| | |
|---|---|
| Blunt-ended, dA-tail DNA | 33 µl |
| Quick ligation reaction buffer (5×) | 10 µl |
| 5 µM DNA linker | 2 µl |
| Quick T4 DNA ligase (NEB) | 5 µl |
| Total volume | 50 µl |

Incubating for 15 min at 20 degrees centigrade;

purifying the DNA samples by a QIAGEN® column, and eluting the samples with 25 µl of sterile dH$_2$O or elution buffer. (QIAGEN is a registered trademark of QIAGEN GmbH GmbH)

Enriching the linker-modified DNA fragment by the PCR pre-amplification;

Preparation of the reaction mixture in Table 4:

TABLE 4

| | |
|---|---|
| DNA | 12.5 µl |
| Phusion DNA polymerase | 25 µl |
| (Phusion DNA polymerase mixture) | |
| PCR primers mixture | 2 µl |
| Ultrapure water | 10.5 µl |
| Total volume | 50 µl |

Implementing amplification by the following PCR experimental protocol:

a. 98 degrees centigrade for 30 s;

b. 18 circulations as below:

98 degrees centigrade for 10 s, 65 degrees centigrade for 30 s, 72 degrees centigrade for 30 s;
  c. 72 degrees centigrade for 5 min;
  d. Incubating at 4 degrees centigrade.

Figure 6:
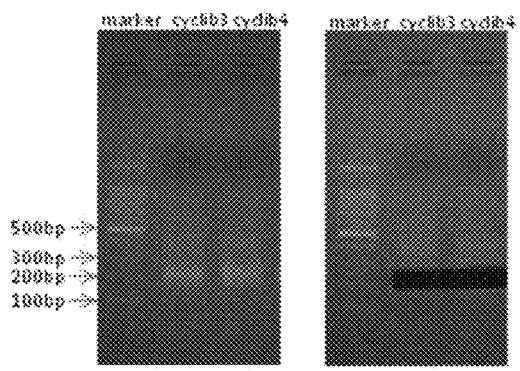
FIG. 6 shows a gel detection result of PCR amplification product according to embodiment 1 of the disclosure.
Figure 7:
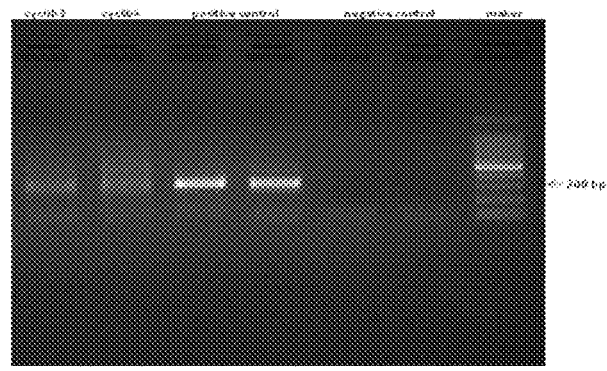
FIG. 7 shows a gel detection result of gel extraction 200 bp target bands according to the embodiment 1 of the disclosure.

Placing the PCR product in 2% of sepharose gel for electrophoresis, the result is shown in FIG. 6, wherein purifying the 2% sepharose gel after pre-amplifying the samples cyclib 3, and cyclib 4; the left represents before gel extraction, and the right represents after gel extraction, the size of the target bands is in line with expectations. And then using a Qiagnen kit to extract 200 bp target bands (as shown in FIG. 7), eluting with 20 μl of elution buffer.

Cyclization Reaction
Construction of cyclization system (Table 5):

TABLE 5

| | |
|---|---|
| DNA template | 12 μl |
| CIRCLIGASE II 10× reaction buffer | 2 μl |
| 50 mM manganese chloride | 1 μl |
| 5M glycine betaine (optimized): | 4 μl |
| CIRCLIGASE II single-strand DNA ligase (100 U) | 1 μl |
| Total volume | 20 μl |

The reaction conditions are as shown in Table 6:

TABLE 6

| | |
|---|---|
| 60° C. | 1 h |
| 80° C. | 10 min |
| 4° C. | incubation |

Enzyme Digestion
Respectively digesting all the cyclization products by Exo III:
the digestion system of Exo III is (as shown in Table 7):

TABLE 7

| | |
|---|---|
| 10× NE Buffer 1 | 1.2 ul |
| Exo III | 1 ul |
| Cyclization product | 10 ul |

Placing the above digestion systems in a PCR instrument to react for 30 min at 37 degrees centigrade.

Implementing column purification for the digestion product after the reaction, dissolving in 30 ul EB, measuring the concentration by Qubit (Invitrogen Company), and the results are as below (as shown in Table 8):

TABLE 8

| Sample | Concentration |
|---|---|
| cyclib3 | 0.3 ng/ul |
| cyclib4 | 2.33 ng/ul |

The back-to-back primers screen at the target region.
Construction of PCR Reaction System (Table 9)

TABLE 9

| | |
|---|---|
| Ultrapure water | 13 or 18 ul |
| AmpliTaq Gold ® 360 Master Mix (2x) | 25 ul |
| Primer F1 | 1 ul |
| Primer R1 | 1 ul |
| DNA | 10 or 5 ul |
| Total | 50 |

Note:
The comparisons are respectively positive (only adding primer, without adding template) and negative (the template is non-cyclized ssCyc Lib).

PCR Reaction Condition (Table 10)

TABLE 10

| | | |
|---|---|---|
| 95° C. | 10 min | 1 cycle |
| 95° C. | 30 s | 30 cycles |
| 55° C. | 30 s | |
| 72° C. | 30 s | |
| 72° C. | 5 min | 1 cycle |

Preparing the PCR product in the former step as library for Illumina high-throughput sequencing, and taking 10 uL of the library to place in 2% of sepharose gel for electrophoresis.

The remained 40 uL of library product is purified by a QIAGEN column to become the final sequencing library.

After controlling quality of the prepared library, the Hiseq 2000 of the Illumina company implements 100 bp double-end sequencing.

Figure 8:
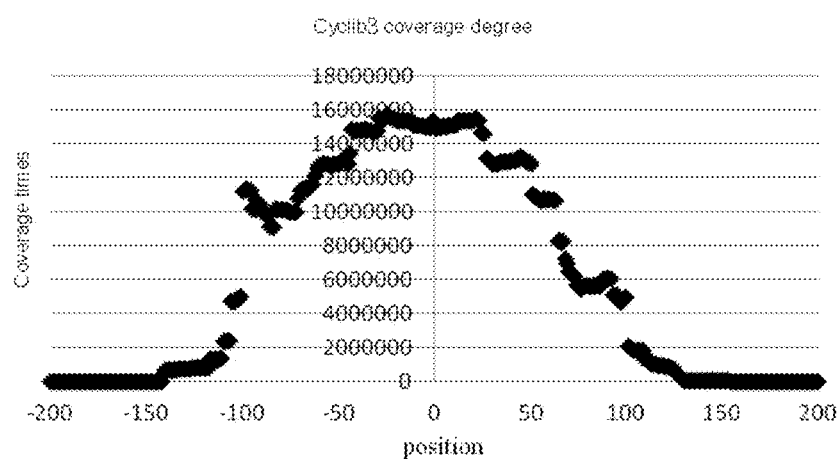
FIG. 8 shows a cyclib3 high-throughput sequencing analysis result according to the embodiment 1 of the disclosure.
Figure 9:
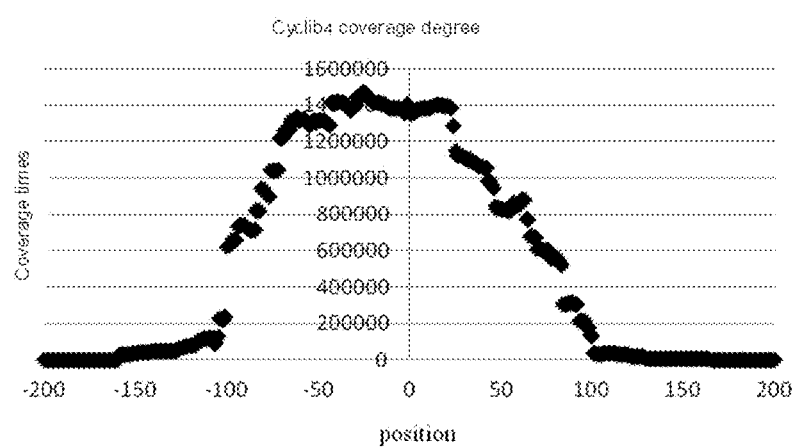
FIG. 9 shows a cyclib4 high-throughput sequencing analysis result according to the embodiment 1 of the disclosure.

Implementing blast search for the high-throughput sequencing sequence, calculating the genome coverage for evaluating the library specificity; intercepting the upstream and downstream 200 bp region of the back-to-back primer, FIG. 8 shows a cyclib3 high-throughput sequencing analysis result according to the embodiment 1 of the disclosure; and FIG. 9 shows a cyclib4 high-throughput sequencing analysis result according to the embodiment 1 of the disclosure; the data result is as shown in Table 11.

TABLE 11

| Sample | PCR primer | Total sequence | Comparable to the genome sequence | Comparable to the genome sequence % |
|---|---|---|---|---|
| cyclib3 the first end | GCTGAGGTGACCCTTGTCTC (SEQ ID NO: 17) | 14288819 | 14273938 | 99.89585563 |
| cyclib3 the second end | CCTCACCATGCTGGAAAGC (SEQ ID NO: 18) | 14288819 | 14274309 | 99.89845207 |
| cyclib4 the first end | GCTGAGGTGACCCTTGTCTC (SEQ ID NO: 19) | 1289834 | 1285618 | 99.67313623 |

TABLE 11-continued

| Sample | PCR primer | Total sequence | Comparable to the genome sequence | Comparable to the genome sequence % |
|---|---|---|---|---|
| cyclib4 the second end | CCTCACCATGCTGGAAAGC (SEQ ID NO: 20) | 1289834 | 1285660 | 99.67639247 |

The embodiment of the disclosure adopts CIRCLIGASE (Epicenter Company) to cyclize the double-strand, however the cyclizaition steps are not limited thereby, for example, the end ligation mediated by T4 DNA ligase, linker-mediated ligation, site specific recombination, cre-loxp cyclization system. The embodiment of the disclosure adopts the design that the close back-to-back primer pair enrich and screen the mutation site, but the enriching and screening steps are not limited thereby, such as the rolling circle amplification mediated by the specific primer.

The DNA fragment detection kit adopted by the disclosure in embodiment 1 includes:

the above DNA extraction reagent, the pre-amplification reagent, the DNA cyclase, the target DNA amplification primer, and the amplification reagent and the corresponding device.

Wherein, the DNA fragment extraction reagent mainly aims at the extraction method of plasma free DNA, urine free DNA, sweat free DNA, saliva free DNA, or the FFPE tissues.

The pre-amplification process needs to be implemented when the extracted DNA fragment has low content, which can be implemented by linker mediated PCR amplification, whole genome amplification and transcription-mediated amplification.

The DNA cyclization can be implemented by single/double-strand DNA ligation mediated by CIRCLIGASE, the ends ligation mediated by T4 DNA ligase, cre-loxp cyclization system, and the recombination cyclization mediated by In-fusion (takara) and the like.

The pre-amplification reagent mainly includes the DNA polymerase and the corresponding buffer, and the whole genome amplification reagent.

The amplification reagent mainly includes the DNA polymerase and the corresponding buffer.

The main reagents include: the plasma DNA solution, T4 DNA phosphorylation buffer (10.times.), 10 mM dNTP mixture, T4 DNA polymerase, T4 DNA phosphorylase, Klenow enzyme, Klenow reaction buffer (10.times.), dATP solution, klenow ex-(3'-5' exonuclease activity deletion), quick ligation reaction buffer (5.times.), Y-shaped DNA double-strand linker, quickT4 DNA ligase (NEB), Phusion DNA polymerase (Phusion DNA polymerase mixture), pre-amplification primer, ultrapure water, CIRCLIGASE II 10.times. reaction buffer, 50 mM manganese chloride, 5 M glycine betaine (optimized), CIRCLIGASE II single-strand DNA ligase, 10.times. NEBuffer 1, Exo III, AmpliTaq Gold 360 Master Mix (2.times.), the back-to-back amplification primer referred in the embodiment 1.

Embodiment 2

1. Linker design

Linkers need to anneal to be double-stranded

```
ssCycADT-1 (SEQ ID NO: 1):
GTCTCATCCCTGCGTGT ssCycADT-2(SEQ ID NO: 2):
pCACGCAGGGTACGTGT
```

The structure of connection products:

```
Top:
                                    (SEQ ID NO: 3)
GTCTCATCCCTGCGTGT (SEQ ID NO: 4)
NNN pCACGCAGGGTACGTGT

Bottom:
                                    (SEQ ID NO: 5)
TGTGCATGGGACGCACp (SEQ ID NO: 6)
NNN TGTGCGTCCCTACTCTG Primers:
ssCycUniprimer-F (SEQ ID NO: 7):
pGTCTCATCCCTGCGTGT ssCycUniprimer-R (SEQ ID NO: 8):
pACACGTACCCTGCGTGT Pre-amplified library structure:
                                    (SEQ ID NO: 9)
pGTCTCATCCCTGCGTGT (SEQ ID NO: 10)
NNN ACACGCAGGGTACGTGT (SEQ ID NO: 11)
CAGAGTAGGGACGCACA (SEQ ID NO: 12)
NNN TGTGCGTCCCATGCACAp
```

The back-to-back amplification primers of target region aim at the kit gene exon 9, wherein, the sequence of kit gene exon 9 is (SEQ ID NO: 21):

```
ATGCTCTGCTTCTGTACTGCCAGTGGATGTGCAGACACTAAACTCATCT

GGGCCACCGTTTGGAAAGCTAGTGGTTCAGAGTTCTATAGATTCTAGTG

CATTCAAGCACAATGGCACGGTTGAATGTAAGGCTTACAACGATGTGGG

CAAGACTTCTGCCTATA^GCCTAT^TTTAACTTTGCATTTAAAGGTAAC

AACAAAG
```

The sequence of the KIT gene exon 9 and the upstream and downstream thereof contain intron (SEQ ID NO: 22)

```
CTCCTCTGCCTTCTCTTCCCCAGTGCTTTTTTCACTCACTAGGTCACCA

AAGTGCTTATTCTTAGACACTTGTAAAAGGACATTTTCTGTTGATTATG

AACCTCTAACTTTGTTTTAAAAGTATGCCACATCCCAAGTGTTTTATGT

ATTTATTTATTTTCCTAGAGTAAGCCAGGGCTTTTGTTTTCTTCCCTTT

AGATGCTCTGCTTCTGTACTGCCAGTGGATGTGCAGACACTAAACTCAT

CTGGGCCACCGTTTGGAAAGCTAGTGGTTCAGAGTTCTATAGATTCTAG
```

-continued

TGCATTCAAGCACAATGGCACGGTTGAATGTAAGGCTTACAACGATGTG

GGCAAGACTTCTGCCTAT^GCCTAT^TTTAACTTTGCATTTAAAGGTAA

CAACAAAGGTATATTTCTTTTTAATCCAATTTAAGGGGATGTTTAGGCT

CTGTCTACCATATCAGTCATGATTTTAAGTTCATTCCAACATTGACCAT

GTCATTTCTGGTAATACATGCATCACACCATACTGTCATCAAACTCACT

A

The sample contains the somatic mutation in this region, and the mutation site is the repeated insertion of GCCTAT.

```
F-1 (SEQ ID NO: 23):
AACGATGTGGGCAAGACTTCTGC

R-1 (SEQ ID NO: 24):
AAGCCTTACATTCAACCGTGCCA
```

2. Taking 1 mL of normal human plasma to extract the plasma free DNA.
3. End-blunting
Preparation of the Reaction Mixture in Table 12

TABLE 12

| plasma DNA solution | 38.5 μl |
|---|---|
| T4 DNA phosphorylation buffer (10x) | 5 μl |
| 10 mM dNTP mixture | 2 μl |
| T4 DNA polymerase | 2 μl |
| T4 DNA phosphorylase | 2 μl |
| Klenow enzyme | 0.5 μl |
| Sterile H$_2$O | 0 μl |
| Total volume | 50 μl |

Incubating for 30 min at 20 degrees centigrade;
purifying the DNA sample by the purification column, and eluting with 42 μl of sterile dH$_2$O or the elution buffer;
adding poly-adenine tail to the 3' end of the DNA fragment.
Preparation of Reaction Mixture in Table 13

TABLE 13

| Blunt-ended DNA | 32 μl |
|---|---|
| Klenow reaction buffer (10x) | 5 μl |
| dATP solution | 10 μl |
| klenow ex-(3'-5'exonuclease activity deletion) | 3 μl |
| Sterile H$_2$O | 0 μl |
| Total volume | 50 μl |

Incubating for 30 min at 37 degrees centigrade;
purifying the DNA samples by the column, and eluting with 25 μl of sterile dH$_2$O or the elution buffer;
connecting the linker to the DNA fragment;
Preparation of the Reaction Mixture in Table 14

TABLE 14

| Blunt-ended, dA-tail DNA | 33 μl |
|---|---|
| Quick ligation reaction buffer (5x) | 10 μl |
| 5 μM DNA linker | 2 μl |
| Quick T4 DNA ligase (NEB) | 5 μl |
| Total volume | 50 μl |

Incubating for 15 min at 20 degrees centigrade;
purifying and recycling the DNA samples by the QIAGEN column, and eluting with 25 μl of sterile dH$_2$O or the elution buffer.
enriching the linker-modified DNA fragment by the PCR pre-amplification.
Preparation of PCR Reaction Mixture in Table 15:

TABLE 15

| DNA | 12.5 μl |
|---|---|
| Phusion DNA polymerase (Phusion DNA polymerase mixture) | 25 μl |
| PCR primers mixture | 2 μl |
| Ultrapure water | 10.5 μl |
| Total volume | 50 μl |

Implementing amplification by the following PCR experimental protocol:
a. 98 degrees centigrade for 30 s;
b. 18 circulations as follows:
98 degrees centigrade for 10 s, 65 degrees centigrade for 30 s, 72 degrees centigrade for 30 s;
c. 72 degrees centigrade for 5 min;
d. Incubating at 4 degrees centigrade.

Placing the PCR product in 2% of sepharose gel for electrophoresis, and then adopting a Qiagnen kit to extract 200 bp target bands, and eluting with 20 μl of elution buffer.
Cyclization Reaction
Construction of Cyclization System (Table 16):

TABLE 16

| DNA template | 12 ul |
|---|---|
| CIRCLIGASE II 10x reaction buffer | 2 ul |
| 50 mM manganese chloride | 1 ul |
| 5M glycine betaine (optimized): | 4 ul |
| CIRCLIGASE II single-strand DNA ligase (100 U) | 1 ul |
| Total volume | 20 |

Reaction Conditions (Table 17)

TABLE 17

| 60° C. | 1 h |
|---|---|
| 80° C. | 10 min |
| 4° C. | incubation |

Enzyme Digestion
Respectively digesting all the cyclization products by Exo III:
the digestion system of Exo III is (as shown in Table 18):

TABLE 18

| 10x NE Buffer 1 | 1.2 ul |
|---|---|
| Exo III | 1 ul |
| Cyclization product | 10 ul |

Placing the above digestion system in a PCR instrument to react for 30 min at 37 degrees centigrade;
implementing column purification for the digestion product after the reaction, dissolving in 30 ul EB.
The back-to-back primers screen at the target region;
Construction of the PCR Reaction System (Table 19)

TABLE 19

| | |
|---|---|
| Ultrapure water | 13 or 18 ul |
| AmpliTaq Gold ® 360 Master Mix (2x) | 25 ul |
| F1 | 1 ul |
| R1 | 1 ul |
| DNA | 10 or 5 ul |
| Total | 50 |

Note:
The comparisons are respectively P (only adding primer, without adding template) and N (the template is non-cyclized ssCycLib).

PCR Reaction Condition (Table 20)

TABLE 20

| | | |
|---|---|---|
| 95° C. | 10 min | 1 cycle |
| 95° C. | 30 s | 30 cycles |
| 55° C. | 30 s | |
| 72° C. | 30 s | |
| 72° C. | 5 min | 1 cycle |

Preparing the PCR product in the former step as the library for Illumina high-throughput sequencing, and taking 10 uL of the library to place in 2% of sepharose gel for electrophoresis:

the remained 40 uL of library product is purified by a QIAGEN column to become the final sequencing library.

After controlling quality of the prepared library, the Hiseq 2000 of the Illumina company implements 36 bp single-end sequencing.

The detection result is shown in Table 21.

TABLE 21

| Sample | Total sequence number | Normal sequence number | Mutation sequence number | Mutation sequence % |
|---|---|---|---|---|
| GIST2 | 2280665 | 1784988 | 11960 | 0.66557 |

The DNA fragment detection kit adopted by the disclosure in embodiment 2 includes:

the above DNA extraction reagent, the pre-amplification reagent, the DNA cyclase, the target DNA amplification primer, and the amplification reagent and the corresponding device.

Wherein, the DNA fragment extraction reagent mainly aims at the extraction method of plasma free DNA, urine free DNA, sweat free DNA, saliva free DNA, or the FFPE tissues.

The pre-amplification process needs to be implemented when the extracted DNA fragment has low content, which can be implemented by linker mediated PCR amplification, whole genome amplification and transcription-mediated amplification.

The DNA cyclization can be implemented by single/double-chain DNA ligation mediated by CIRCLIGASE, the ends ligation mediated by T4 DNA ligase, cre-loxp cyclization system, and the recombination cyclization mediated by In-fusion (takara) and the like.

The pre-amplification reagent mainly includes the DNA polymerase and the corresponding buffer, and the whole genome amplification reagent.

The amplification reagent mainly includes the DNA polymerase and the corresponding buffer.

The main reagents include: the plasma DNA solution, T4 DNA phosphorylation buffer (10.times.), 10 mM dNTP mixture, T4 DNA polymerase, T4 DNA phosphorylase, Klenow enzyme, Klenow reaction buffer (10.times.), dATP solution, klenow ex-(3'-5' exonuclease activity deletion), quick ligation reaction buffer (5.times.), Y-shaped DNA double-strand linker, quick T4 DNA ligase (NEB), Phusion DNA polymerase (Phusion DNA polymerase mixture), pre-amplification primer, ultrapure water, CIRCLIGASE II 10.times. reaction buffer, 50 mM manganese chloride, 5 M glycine betaine (optimized), CIRCLIGASECircLigaso II single-stand DNA ligase, 10.times. NEBuffer 1, Exo III, AmpliTaq Gold 360 Master Mix (2.times.), the back-to-back amplification primer mentioned in the embodiment 2.

From the experimental results of the embodiment 1 and the embodiment 2, it can see that the target DNA fragment can be detected by adopting the plasma DNA solution by the method and kit of the disclosure, but cannot be directly detected by the PCR in the prior art.

The above is only the preferred embodiment of the disclosure, but not intended to limit the disclosure, for those skilled in the field, the disclosure can have various changes and modifications. Any modifications, equivalent replacement and improvements within the spirits and principle of the disclosure shall fall within the protection scope of the disclosure.

What is claimed is:

1. A DNA fragment detection method, comprising the steps of:
designing primers based on a test site adjacent sequence or a test region adjacent sequence of a DNA fragment, wherein the primers are a primer pair comprising of adjacent primers which extend backwards and the primers of the primer pair which extend backwards are all located on the 5' end 3' end of the test site or the test region of the DNA fragment;
cyclizing the DNA fragment to obtain a cyclized DNA;
implementing PCR amplification for the cyclized DNA by using the primers; and
detecting a product of the PCR amplification,
wherein the DNA fragment refers to a short fragment DNA which is formed by natural random fragmentation of biological genomic DNA, and has a length of 20 bp to 2000 bp.

2. The method according to claim 1, wherein the interval between the primers of the primer pair which extend backwards is 0-½ of the total base pairs of the DNA fragment.

3. The method according to claim 2, wherein the interval between the primers of the primer pair which extend backwards is 0-50 base pairs.

4. The method according to claim 3, wherein the interval between the primers of the primer pair which extend backwards is 0-10 base pairs.

5. The method according to claim 1, wherein the bases on the 5' end of the primers of the primer pair which extend backwards are overlapped partly.

6. The method according to claim 1, wherein before cyclizing the DNA fragment, the method further includes a step of pre-amplifying the DNA fragment.

7. The method according to claim 1, wherein the DNA fragment comprises of the plasma free DNA, urine free DNA, sweat free DNA, saliva free DNA, or the DNA extracted from formalin-fixed and paraffin-embedded tissues.

8. The method according to claim 1, wherein the test site or the test region of the DNA fragment include insertion, deletion, substitution or fusion gene mutation.

9. A DNA fragment detection method, comprising the steps of:
- designing one primer according to a test site adjacent sequence or a test region adjacent sequence of the DNA fragment, the primer located on the 5' end or 3' end of the test site or the test region of the DNA fragment;
- cyclizing the DNA fragment to obtain a cyclized DNA;
- implementing PCR amplification for the cyclized DNA by using the primer; and
- detecting the PCR amplification product, the DNA fragment refers to a short fragment DNA which is formed by natural random fragmentation of biological genomic DNA, and has the length of 20-2000 bp.

\* \* \* \* \*